US012678748B2

(12) United States Patent
Bauer

(10) Patent No.: US 12,678,748 B2
(45) Date of Patent: Jul. 14, 2026

(54) REVERSING FLOW APPARATUS

(71) Applicant: Walter Jacob Bauer, Baden (CA)

(72) Inventor: Walter Jacob Bauer, Baden (CA)

( * ) Notice: Subject to any disclaimer, the term of this patent is extended or adjusted under 35 U.S.C. 154(b) by 1015 days.

(21) Appl. No.: 17/781,031

(22) PCT Filed: Dec. 5, 2020

(86) PCT No.: PCT/CA2020/000132
§ 371 (c)(1),
(2) Date: May 30, 2022

(87) PCT Pub. No.: WO2021/108888
PCT Pub. Date: Jun. 10, 2021

(65) Prior Publication Data
US 2022/0410089 A1      Dec. 29, 2022

Related U.S. Application Data

(60) Provisional application No. 62/944,813, filed on Dec. 6, 2019.

(51) Int. Cl.
B01F 23/41 (2022.01)
A61L 2/10 (2026.01)
(Continued)

(52) U.S. Cl.
CPC ............ B01F 23/4145 (2022.01); A61L 2/10 (2013.01); B01D 17/04 (2013.01); B01F 23/237612 (2022.01); B01F 23/237613 (2022.01); B01F 23/23762 (2022.01); B01F 23/23764 (2022.01); B01F 25/4318 (2022.01); B01F 25/431972 (2022.01); B01F 35/181 (2022.01)

(58) Field of Classification Search
CPC ............ B01F 25/431972; B01F 27/111; B01F 27/1152; B01F 27/112; B01F 11/1125; B01F 11/11252; B01F 25/43197; B01F 23/4145; B01F 25/431; B01F 25/4318
USPC ........................................................... 366/253
See application file for complete search history.

(56) References Cited

U.S. PATENT DOCUMENTS

| | | | | |
|---|---|---|---|---|
| 687,182 | A | * | 11/1901 | Franklin ............... F04D 29/326 |
| | | | | 416/189 |
| 3,352,659 | A | * | 11/1967 | Villem .................. C03B 5/1875 |
| | | | | 65/135.1 |

(Continued)

FOREIGN PATENT DOCUMENTS

| | | |
|---|---|---|
| CN | 1780691 A | 5/2006 |
| CN | 105592916 A | 5/2016 |

(Continued)

*Primary Examiner* — Elizabeth Insler
(74) *Attorney, Agent, or Firm* — Perry + Currier

(57) ABSTRACT

A reversing flow apparatus comprising a chamber having a series of two or more sequential rings mounted on a shaft extending axially through the chamber, the rings being separated by a space, each ring comprising a circumference and one or more S-shaped members extending from a point in the circumference to another point in the circumference and across a center of the ring, the two or more sequential rings being mounted along the shaft in a twist arrangement such that at least one ring In the apparatus has its S-shaped member in a forward-facing position and at least one ring in the apparatus has its S-shaped member in a reverse-facing position.

26 Claims, 5 Drawing Sheets

(51) Int. Cl.

| | | |
|---|---|---|
| *B01D 17/04* | (2006.01) |
| *B01F 23/237* | (2022.01) |
| *B01F 25/431* | (2022.01) |
| *B01F 35/00* | (2022.01) |

(56) References Cited

U.S. PATENT DOCUMENTS

| | | | |
|---|---|---|---|
| 4,008,072 A | 2/1977 | Kuhn et al. | |
| 4,893,941 A * | 1/1990 | Wayte | B01F 27/111 |
| | | | 366/265 |
| 5,868,495 A | 2/1999 | Hidalgo | |
| 5,887,977 A | 3/1999 | Morikawa | |
| 2005/0286343 A1 | 12/2005 | Boutet et al. | |
| 2006/0175254 A1 | 8/2006 | Bauer | |
| 2011/0151524 A1 | 6/2011 | Gordon et al. | |
| 2013/0008857 A1 | 1/2013 | Foster | |
| 2013/0021868 A1 | 1/2013 | Doolin et al. | |
| 2016/0236158 A1 | 8/2016 | Bauer | |
| 2017/0205070 A1 | 7/2017 | Ryon | |
| 2017/0266717 A1* | 9/2017 | Cassinath | B01F 27/902 |
| 2018/0134583 A1 | 5/2018 | Bauer | |
| 2018/0339277 A1 | 11/2018 | Mochizuki | |

FOREIGN PATENT DOCUMENTS

| | | | |
|---|---|---|---|
| CN | 206566856 U | 10/2017 |
| CN | 109053412 A | 12/2018 |
| CN | 110191752 A | 8/2019 |
| EA | 201270221 A1 | 8/2012 |
| JP | 2008018330 A | 1/2008 |
| JP | 2008284552 A | 11/2008 |
| JP | 2010022927 A | 2/2010 |
| JP | 4882024 B2 | 2/2012 |
| JP | 2016536139 A | 11/2016 |
| JP | 2018516172 A | 6/2018 |
| JP | 3220785 U | 4/2019 |
| KR | 101376971 B1 | 3/2014 |
| KR | 20160067909 A | 6/2016 |
| RU | 1142499 A1 | 2/1985 |
| RU | 1159613 A1 | 6/1985 |
| RU | 1212536 A1 | 2/1986 |
| RU | 2009687 C1 | 3/1994 |
| RU | 2422493 C1 | 6/2011 |
| RU | 2536583 C2 | 12/2014 |
| RU | 2693136 C9 | 10/2019 |
| WO | WO-2014119775 A1 | 8/2014 |

* cited by examiner

REVERSING FLOW APPARATUS

FIELD OF THE INVENTION

The present disclosure relates to a reversing flow apparatus device for mixing two or more solutions or mixing one
or more solutions with one or more solutes and to systems
and methods of producing mixed liquid solutions. The
present disclosure relates also to processing emulsions with
the reversing flow apparatus of the present disclosure.

BACKGROUND OF THE INVENTION

In the marketplace today the static mixers do not cut and
redirect the flow of liquid solutions from laminar to turbulent flow. The liquid remains partially laminar therefore they
are inefficient on creating a true new homogeneous mix.
They also have dead spots within them that have little to no
flow allow debris to collect.

Oil emulsions are broken using solvents, ultrasound and/
or heat distillation extraction. It would be advantageous to
have a device requires no heat, ultrasound or solvents to
break inter and intra molecular bonds and separate water
from an oil emulsion.

SUMMARY OF THE INVENTION

Within the present disclosure, an apparatus for obtaining
a mixture of liquids or for obtaining a mixture of liquid(s)
and solid(s) or a mixture of liquid(s) and gas(es), and systems and methods enabling the generation of said mix-
tures.

In one embodiment, the present disclosure provides for a
reversing flow apparatus comprising a chamber having a
series of two or more sequential rings mounted on a shaft
extending axially through the chamber, the rings being
separated by a space, each ring comprising a circumference
and one or more S-shaped members extending from a point
in the circumference to another point in the circumference
and across a center of the ring, the two or more sequential
rings being mounted along the shaft in a twist arrangement
such that at least one ring in the apparatus has its S-shaped
member in a forward-facing position and at least one ring in
the apparatus has its S-shaped member In a reverse-facing
position.

In embodiments of the reversing flow apparatus of the
present disclosure, the spiral apparatus includes a housing
having an inflow portion for receiving one or more untreated
liquids, a treatment portion containing the chamber for
treating the one or more untreated liquid, and an outflow
portion for releasing the treated one or more liquids.

In embodiments of the reversing flow apparatus of the
present disclosure, the one or more rings are made of a metal
or a combination of metals.

In embodiments of the reversing flow apparatus of the
present disclosure, the rings are made of stainless-steel
containing molybdenum (Mo).

In embodiments of the reversing flow apparatus of the
present disclosure, the rings are made of a metal alloy
comprising about 0.5 wt. % or more molybdenum, about 1.0 wt. % or more molybdenum, about 1.5 wt. % or more
molybdenum or from about 3.0 wt. % to about 4.0 wt. %
molybdenum.

In embodiments of the reversing flow apparatus of the
present disclosure, the space is 15 cm or less.

In another embodiment, the present disclosure provides
for a system for treating liquid solutions or emulsion, the system including a source of the liquid solution or emulsion
and a reversing flow apparatus according an embodiment of
the present disclosure, the inflow portion of the reversing
flow apparatus being operatively connected to the source.

In embodiments, the system further comprises at least one
of a filtration device, a UV sterilizer and a Z potential crystal
generator, wherein the reversing flow apparatus, the source
and the at least one of the filtration device, the UV sterilizer
and the Z potential crystal generator are in liquid commu-
nication with one another.

In embodiments, the system further comprises a filtration
device, a UV sterilizer and a Z potential crystal generator,
wherein the reversing flow apparatus, the source, the filtra-
tion device, the UV sterilizer and the Z potential crystal
generator are in liquid communication with one another.

In embodiments, the system comprises multiple reversing
flow apparatuses according to embodiments of the present
disclosure.

In another embodiment, the present disclosure relates to a
method producing a mixed solution of liquids or of one or
more liquids with one or more solids, the method comprising
passing the liquids to be mixed or the one or more liquids
and the one or more solids to be mixed through the reversing
flow apparatus according to an embodiment of the present
disclosure, thereby producing the mixed solution.

In embodiments of the method of producing a mixed
solution, the one or more liquids includes a gas.

In embodiments of the method of producing a mixed
solution, the one or more liquids are optionally passed,
before or after the apparatus, through at least one filtration
system.

In embodiments of the method of producing a mixed
solution, the gas include nitrogen, oxygen, carbon dioxide,
ozone, ethanol, methanol, hydrogen or combinations
thereof.

In another embodiment, the present disclosure relates to a
method of converting laminar flow to turbulent flow, the
method comprising passing a liquid with laminar flow
through the reversing flow apparatus according to an
embodiment of the present disclosure.

In another embodiment, the present disclosure proves for
a liquid or emulsion processed with an apparatus of the
present disclosure.

In another embodiment, the present disclosure relates to a
method of breaking an oil-in-water emulsion, the method
comprising passing the oil-in-water emulsion though a
reversing flow apparatus of the present disclosure to obtain
a processed material whereby a separate aqueous phase and
oil phase is produced.

In one embodiment of the method of breaking an on-in-
water emulsion, the method further comprises pyrolyzing
the oil-in-water emulsion to obtain a derivative, and wherein
the method comprises passing the derivative through the
reversing flow apparatus instead of the oil-in-water emul-
sion.

In another embodiment of the method of breaking the
oil-in-water emulsion, the oil-in-water emulsion is oily
wastewater, a petroleum feedstock or a part of a secondary
oil recovery system.

In another embodiment, the present disclosure relates to a
method of lowering the viscosity of liquid solution or
emulsion containing oil, the method comprising passing the
liquid solution or emulsion containing oil through a revers-
ing flow apparatus of the present disclosure to obtain a
processed material having lower viscosity than the liquid
solution or emulsion containing oil, thereby lowering the
viscosity of the liquid solution or emulsion containing oil.

In another embodiment, the present disclosure relates to a method of lowering the boiling point of an original liquid source having boiling point of an original liquid source having boiling kerogens, long-chain hydrocarbons or a mixture thereof, the method comprising passing the original liquid source through a reversing flow apparatus of the present disclosure to obtain a treated material, wherein the boiling point of the original liquid source is higher than the boiling point of the treated liquid.

In another embodiment, the present disclosure relates to a method of cracking a liquid comprising passing the liquid through a reversing flow apparatus of the present disclosure to obtain a cracked liquid.

In embodiments of the method of cracking a liquid, the cracked liquid contains contain more hydrocarbons having shorter carbon chain species relative to the liquid.

In embodiments of the method of cracking a liquid, the method is devoid of solvents.

In embodiments of the method of cracking a liquid, the liquid is an emulsion, a petroleum feedstock or a part of a secondary oil recovery system.

In another embodiment, the present disclosure relates to a method of treating Crohn's Disease, a neuropathy or reducing inflammation of knee joints in a subject, comprising administering to the subject a liquid processed through a reversing flow apparatus of the present disclosure.

In another embodiment, the present disclosure relates to a use of liquid processed through a reversing flow apparatus of the present disclosure for the treatment of Crohn's Disease, a neuropathy or for reducing inflammation of joints.

BRIEF DESCRIPTION OF THE DRAWINGS

The following figures illustrate various aspects and preferred and alternative embodiments of the disclosure.

DESCRIPTION OF THE INVENTION

Definitions

Figure 1:
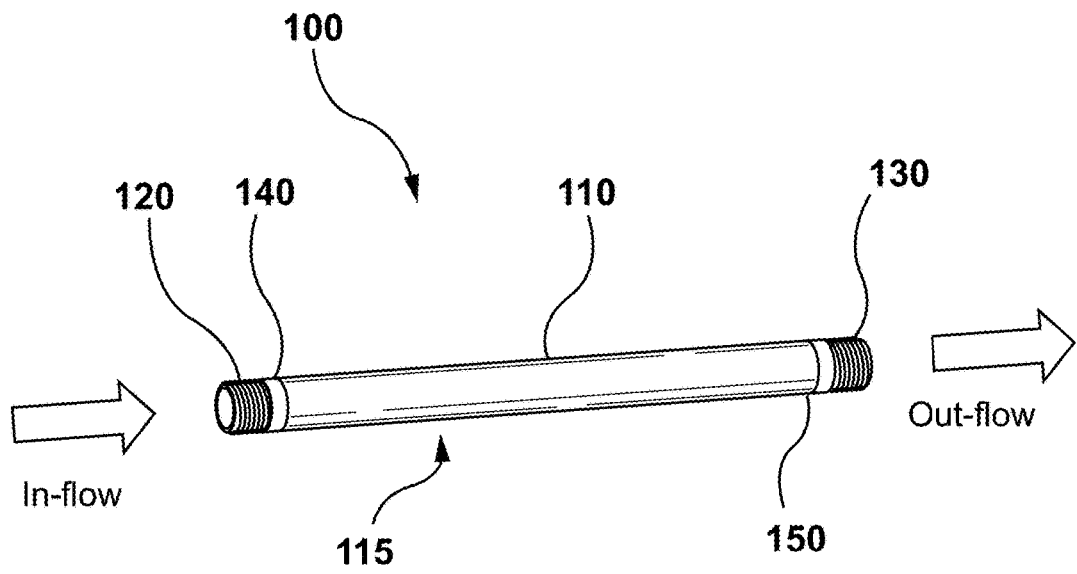
FIG. 1. Perspective view of an outside of a reverse flow apparatus according to one embodiment of the present disclosure.

Unless defined otherwise, all technical and scientific terms used herein have the same meaning as commonly understood by one of ordinary skill in the art to which this disclosure belongs. Also, unless indicated otherwise, except within the claims, the use of "or" includes "and" and vice versa. Non-limiting terms are not to be construed as limiting unless expressly stated or the context clearly indicates otherwise (for example "containing", "including", "having" and "comprising" typically indicate "including without limitation"). Examples of limiting terms include "consisting of" and "consisting essentially of". Singular forms including in the claims such as "a", "an" and "the" include the plural reference unless expressly stated otherwise.

The term "fluid" includes liquids and/or gases.

The term "liquid" is used to include liquid solutions and/or emulsions (oil-in-water, or water-in-oil emulsions) and/or liquids containing a single component.

The term "waste oil" used herein includes a fossil fuel waste oil, a waste edible oil, and a mixture thereof and to solution and emulsions containing waste oil.

The terms "treat," "treating," and "treatment" when used in relation to treating a disease, refer to a method of alleviating or abating the disease and/or its attendant symptoms.

In order to aid in the understanding and preparation of the within disclosure, the following illustrative, non-limiting, examples are provided.

a. Overview

The inventive static, reversing flow apparatus, system and method of the present disclosure effectively converts the flow of a liquid from laminar to a turbulent flow. The inventive apparatus, system and method of the present disclosure effectively produces mixtures of liquids, or liquids with solids or liquids with gases, and without requiring the use of catalysts toxic or harmful additives or chemicals. In some embodiments, the term "mixture" is used to refer to the output of the apparatus of the present disclosure. The system and process may be implemented in a stationary, installed unit, or in a portable unit. The inventive system may also be retrofitted in existing liquid solution distribution systems, such as water distribution systems. Although several specific embodiments are described. It will be apparent that the disclosure is not limited to the embodiments illustrated, and that additional embodiments may also be used. The liquid mixtures produced by the methods of the present disclosure are highly effective in a variety of application as it will be described herein below. The apparatus, systems and methods of the present disclosure do not require external air or gas to produce the mixtures.

b. Reversing Flow Apparatus

With reference to the embodiments illustrated in FIGS. 1 to 6, the apparatus or device 100 of the present disclosure includes a housing or body 110 of the apparatus 100 having an inflow portion 140 for receiving one or more liquids (the untreated liquids) with or without one or more solids or gases, an out-flow portion 150 for releasing the mixture (the treated liquid or liquids), and a treatment portion 115 between the inflow 140 and outflow 150 for treating the one or more liquids with or without one or more solids or for treating emulsions, such as oil-in-water or water-in-oil emulsions. For example, tap water can contain chloride and fluoride, wastes can contain water and oils, and so forth. The apparatus or device 100 of the present disclosure may also be referred to as a static apparatus because it has no moving parts.

In embodiments, the housing 110 takes a substantially tubular form. The inlet 140 and outflow 150 portions may include a threaded boss 120 and 130 at each end. The housing 110 and bosses 120 and 130 are preferably made of a substantially inert material. In embodiments examples of such inert material include polymers such as polyvinyl chloride (pvc).

Figure 5A:
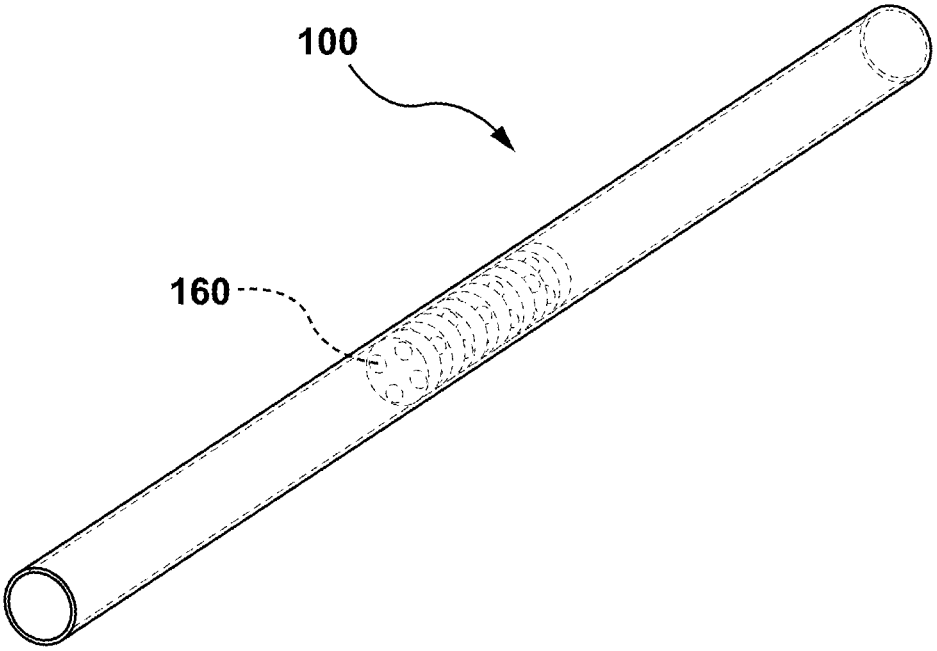
FIG. 5A. Illustration of a set-up of 7 rings within a reverse flow apparatus according to one embodiment.
Figure 5B:
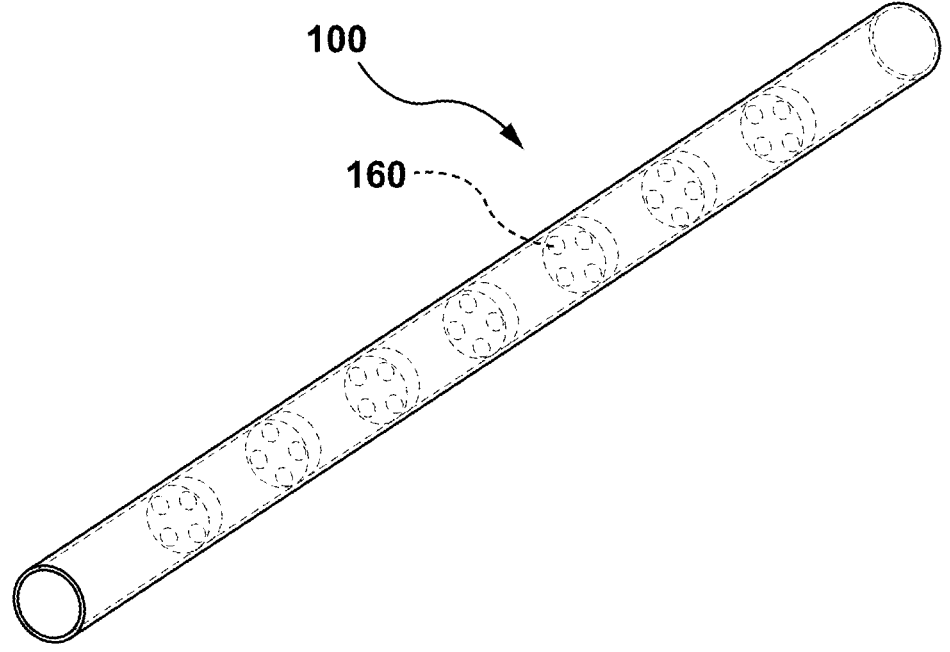
FIG. 5B. An embodiment of a set-up of 7 rings within the same reverse flow apparatus illustrated in FIG. 5A.
Figure 6:
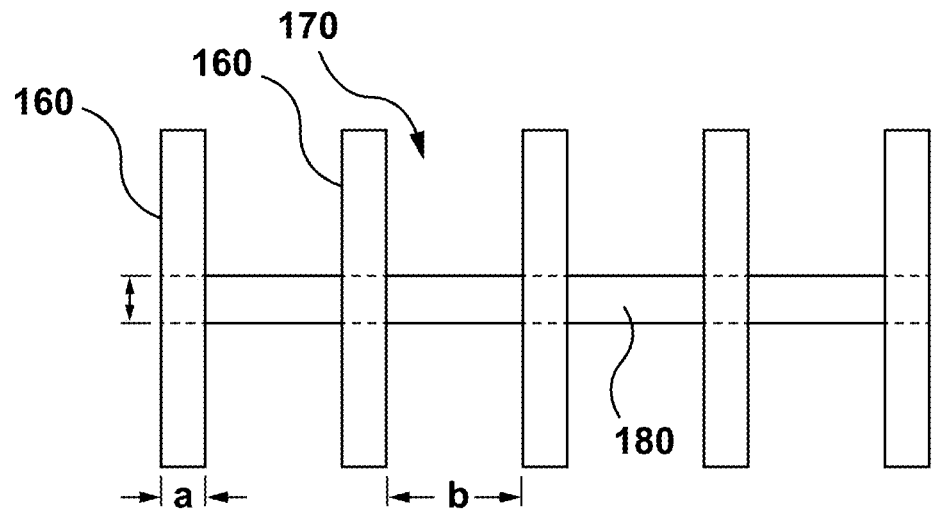
FIG. 6. Side view of a reverse flow apparatus according to one embodiment of the present disclosure.

The treatment portion 115 of the apparatus includes a series of ring elements 160 sequentially disposed along a longitudinal axis of the housing 110 and are interposed between the inflow and the outflow portions of the spiral apparatus 100 as shown in FIGS. 2, 5A-5B and 6. The number of rings in the spiral apparatus 100 will depend on the length of the housing 110. In embodiments, between 2 and 30 spaced apart rings 160 may be used. More than 30 spaced apart rings 160 may also be used in longer housings. Each ring element 160 may take the form of a disc. In embodiments, the ring elements 160 are supported upon or mounted on a central rod or shaft 160. The ring element 160 may include opposite sides or walls 161, 162, and a peripheral or side wall along the circumference 163 of the ring element 160. One side 161 of the ring element 160 faces the inflow portion and the opposite side 162 faces the outflow portion of the apparatus. The peripheral wall 163 extends between opposite shear walls 161, 162. The ring-like elements 160 may be held in spaced relation to each other. The elements 160 may be separated from one another by a space 170. In embodiments, the space 170 that separates elements 160 may vary depending on the length and/or diameter of the housing 110. The bigger the diameter and/or longer the length, the longer the space 170 may be. For example, for a housing 110 having a diameter of 8 inches (about 20.32 cm) or less, the space 170 may be, for example, between about 0.1 inches (about 0.25 cm) to about 12 inches (about 30.5 cm). In embodiments, the space is about 30 cm or less. In embodiments, the space is 15 cm or under 15 cm. A 60-inch (about 152.4 cm) diameter housing 110 may include spaces 170 that are over 8 inches (about 20.32 cm). FIGS. 5A-5B illustrate different set ups of the rings 160 within the same apparatus 100.

In embodiments, each element 160 includes or receives at least one curved member 310, which can take an S-shape or serpentine-shape. The S-shaped member 310 extends from one point in the circumference 163 of element 160 to another point in the circumference 163, while crossing the center 169 of the ring element 160, thereby creating apertures 311 between S-shaped members 310 of one ring 160. In embodiments, each S-shaped member 310 includes edges 167. In embodiments, the edges 167, which in embodiments have a scallop design, are sharp. Each element 160 can include at least one S-shaped member 310. In embodiments, the element 160 includes 2 co-planar S-shaped member 310. In embodiments, element 160 may also include more than 2 (i.e. 3, 4, 5 and so forth) S-shaped members. Preferably the disc-like elements including the S-shaped member 310 are made laser cut.

Each element 160 has a width "a". In embodiments, the width "a" of each disc-like element 160, is about one half or less of the distance "b" between two consecutive ring elements 160. In embodiments, the center 169 of each element 160 includes an aperture 168 to receive the shaft 180. The ring element Illustrated in FIG. 3 does not show an aperture to receive the shaft 180, however, this illustration is just an example, and an aperture should be present to receive the shaft.

Figure 2:
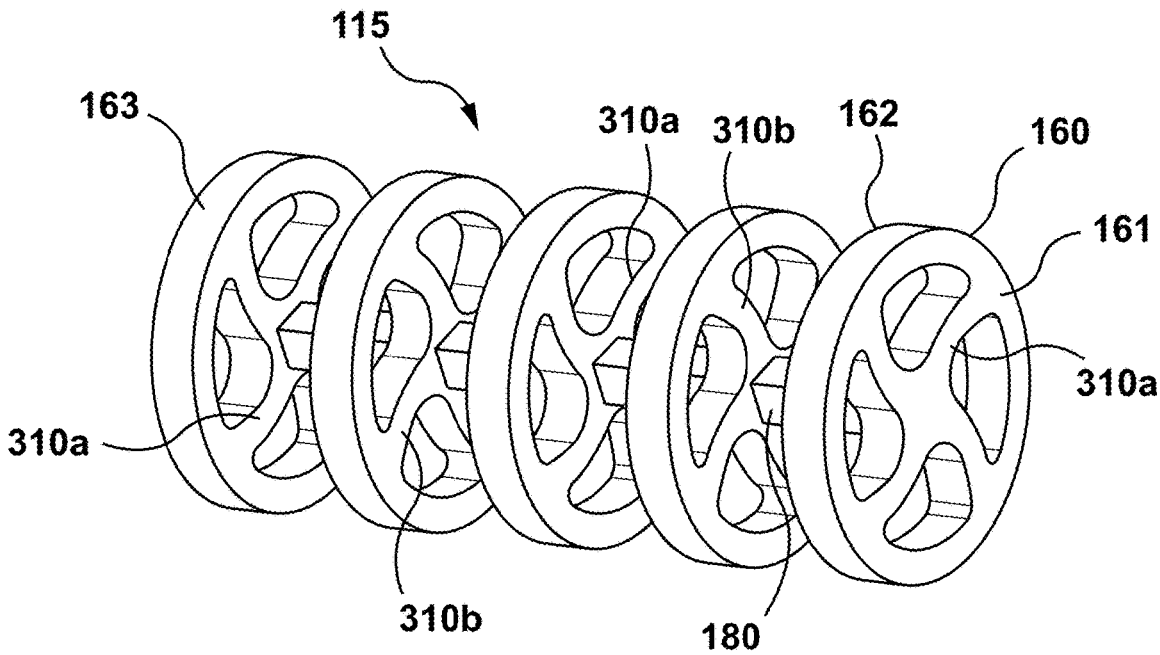
FIG. 2. Perspective view of an inside of the treatment portion of a reverse flow apparatus according to one embodiment of the present disclosure.
Figure 3:
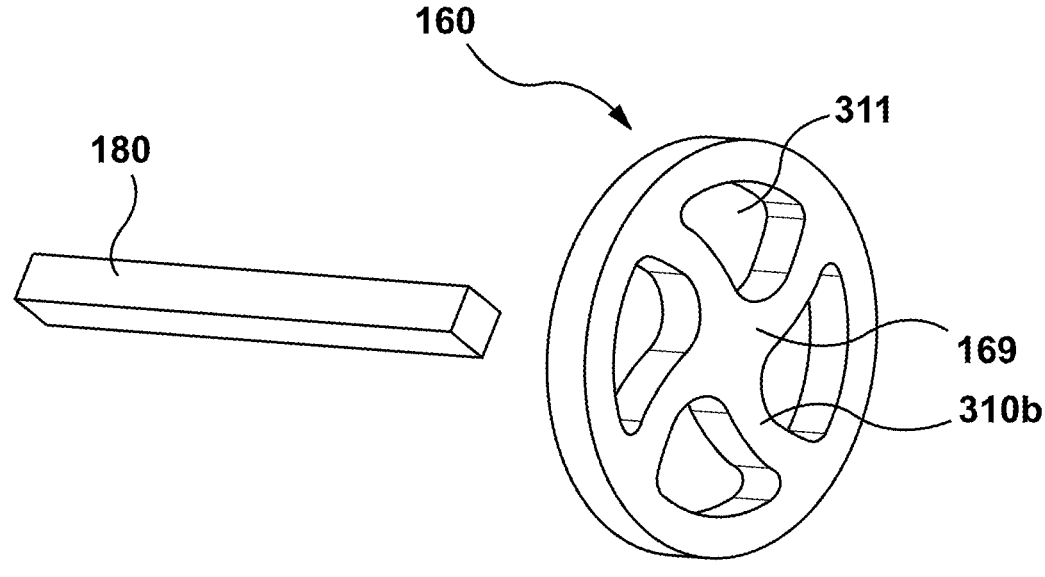
FIG. 3. Perspective view of a ring element and a shaft of a reverse flow apparatus according to one embodiment of the present disclosure.
Figure 4:
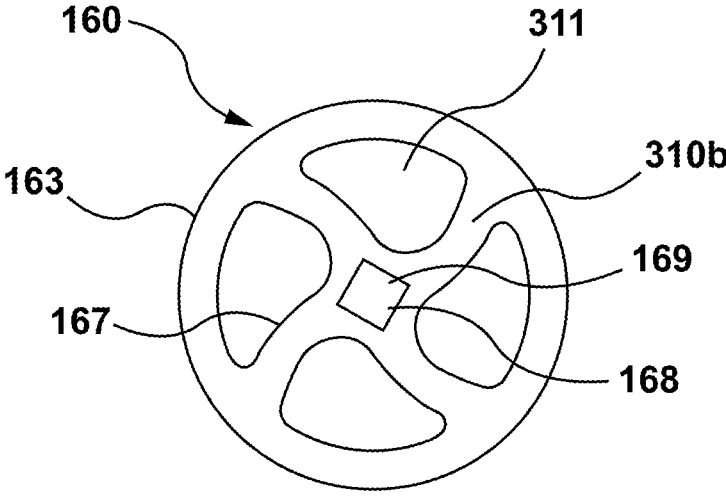
FIG. 4. Front view of a ring element of a reverse flow apparatus according to one embodiment of the present disclosure.

The axially successive rings 160 are arranged along the rod 180. In one embodiment, the elements 160 are arranged on rod 180 in a twister or spiral arrangement, such that at least one ring 160 has its S-shaped member 310 in a forward-facing position (310a) and at least one ring has its S-shaped member in a reverse-facing position (310b) (i.e. at least one ring element is inverted or flipped relative to another ring element in the apparatus). FIG. 2 illustrates an alternating pattern in which a ring having the S-shaped member 310 in a forward-facing position (310a) is followed by ring having a ring with the S-shaped member in a reverse-facing position (310b). Having the members 310 arranged in a spiral arrangement serves to rotate the flow of the incoming liquid and to increase shear force by reversing the flow of the liquids, solutions or emulsions being treated, hence the apparatus 100 of the present disclosure may be referred to as a reversing flow apparatus. However, it should be understood that the present disclosure also covers a situation in which two or more rings with the same direction of the S-shaped member 310 are next to one another as long as at least one ring in the housing 110 has the reverse direction S-shaped member 310.

In embodiments, each ring 160 is disposed substantially perpendicular to the flow of the untreated liquid or fluid within the housing 110, such as the elements 160 substantially reduces any direct liquid or fluid flow through the housing 110 and as a result the liquid or fluid flow passes through the apertures 311 in each of the rings 160. Due to the twist arrangement of the S-shaped members 310, the liquid/fluid flow between the rings 160 is turbulent and by virtue of the differing cross-sectional areas of the apertures 311 in each ring 160, the width of the rings 160, and the space 170 between the rings 160 the liquid/fluid is caused to accelerate and decelerate on its passage through the housing 110 to ensure a turbulent flow over the surfaces of the discs 160.

In embodiments, the rings 160 are manufactured from a single metal. Preferably the ring elements 160 are made of a corrosion resistant metal. Preferably, the ring elements are made from a nonmagnetic stainless steel 300 series, such as 316L, 317L or 904L or any stainless steel that contains molybdenum (Mo). Preferably the elements 160 are laser cut, machined cut or cut with a nonionic process such as water jet cutting in order to help maximize the properties of the metallurgy.

In embodiments, the elements 160 are made of a corrosion resistant metal or alloy containing from about 0.5 wt. % to about 4 wt. % molybdenum or more. In certain embodiments, it is envisioned that the elements may contain up to 5 wt. % molybdenum or up to 10 wt. % molybdenum. The elements 160 may be made from a stainless steel 300 series alloy such as 316L or 317L and also 904L. According to certain aspects of the present teaching, the 300 series alloy includes a minimum amount of molybdenum. In certain embodiments, the minimum amount of molybdenum is about 0.5 wt. % of the total weight of the alloy. In further embodiments, the minimum amount of molybdenum is greater than 3 wt. %, or about 4 wt. % of the total weight of the alloy. In further embodiments, the minimum amount of molybdenum is greater than 4 wt. % of the total weight of the alloy. In certain embodiments, the elements 160 are made from stainless steel 317L or 904L.

At least one of surface of the elements 160 may be machined or polished to remove forging scale from the casting process. In certain embodiments, the surfaces may be machined or polished to remove forging scale and in other embodiments, the surfaces are machined or polished to remove forging scale from the casting process. For example, In certain cases, the thickness of the elements is reduced from ⅝ inch to ¼ inch (about 1.6 cm to about 0.6 cm) by machining and/or polishing thereby exposing the bare metal of the disc-like metal.

Molybdenum-Activated Liquid Producing System

Molybdenum is an essential trace mineral found in foods such as milk, cheese, cereal grains, legumes, nuts, leafy vegetables, and organ meats.

Molybdenum is most used for molybdenum deficiency. It is also used for cancer of the esophagus, other types of cancer, Wilson disease, and other conditions, but there is no good scientific evidence to support these uses.

The molybdenum-activated treated liquid of the present disclosure may condition surfaces by removing oils, enzymes, phenols, and other impurities within the liquid. The molybdenum-activated liquid improves the solvency of the liquid and produces a new type of lubricant which serves to deter biofilm attachment to surfaces. The combination of the effects above creates a sanitized surface/system.

c. System

The system of the present disclosure may be constructed in a variety of different embodiments and may be employed in connection with creating mixtures of liquids or of liquid(s) and solid(s) and of processing liquids.

In embodiments, the inventive system includes at least one apparatus 100 of the present disclosure. The system may include one, two, three or more apparatuses 100 of the present disclosure. If more than one apparatus 100 are included, the apparatuses 100 may be disposed in series one next to another, or they may alternate between other components of the system. In another embodiment, the system includes a source of liquid and a treatment module including an apparatus 100 of the present disclosure.

Polar and non-polar liquid, hydrophilic and lipophilic liquids, including solutions and emulsions, may be used as source liquid or fluid for the inventive system and treated to create a mixture or to create a processed liquid/emulsion or liquid solution or emulsion. As such, the source may include oils, alcohols, water, solvents, fuels, surfactants, gels, carbohydrates, oil wastes, petroleum, a part of a secondary oil recovery, water wastes and so forth, or combinations of any one of oils, alcohols, water, solvents, fuels, surfactants, gels, carbohydrates, oil wastes, water wastes.

Figure 7:
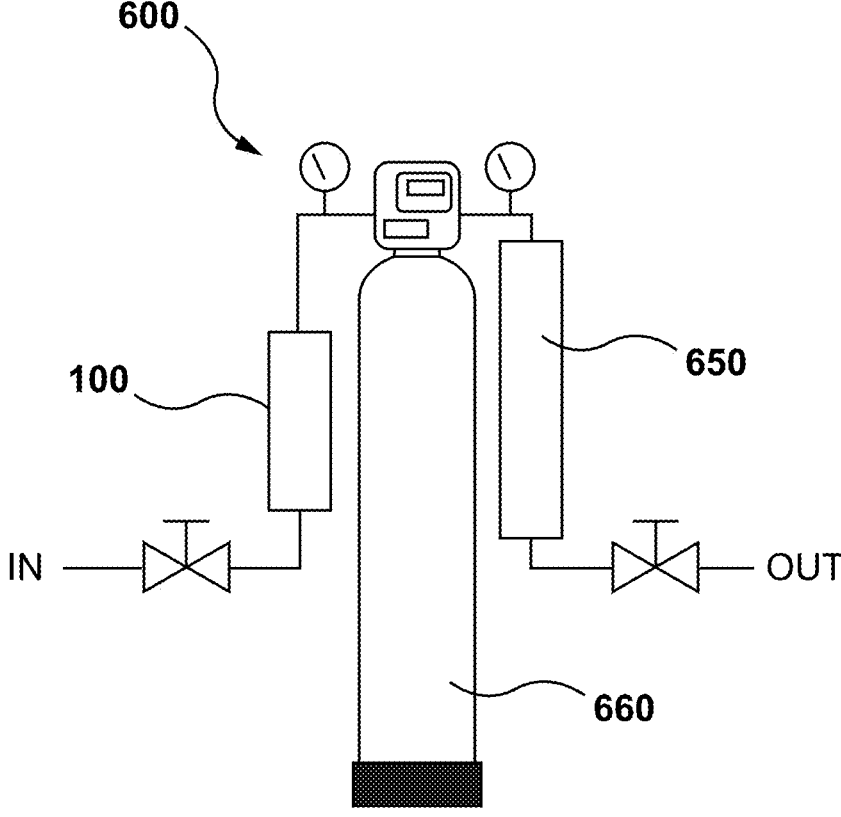
FIG. 7. Graph illustrating a system containing a reverse flow apparatus in accordance to one embodiment of the present disclosure.

With reference to FIG. 7, the system 600, in embodiments, includes an optional source liquid pre-treatment system (not shown), an apparatus 100 of the present disclosure, optionally at least one filtration device 660, and an optional UV sterilizer 650. The apparatus 100, the filter 660 and the UV sterilizer 650 are in liquid communication with one another and are connected by way of a conduit system. The conduit system may include, for example, pipes, hoses, tubes, channels, and the like.

The source liquid or source fluid, such as water or tap water, solutions, emulsions, oils, alcohols, liquid wastes and so forth, is supplied from any suitable source (for example a faucet, a tank or container) and the liquid/fluid may be stored in a reservoir, or may be supplied continuously or intermittently from any source. The composition of source liquid may be tested and, if necessary, additional minerals and other constituents may be added. The source liquid may also be treated, prior or subsequent to holding in reservoir, in pre-treatment system to substantially remove unwanted contaminants that may interfere with the treatment process, such as debris, oil-containing constituents, and the like.

Source liquid may be added continuously or intermittently to the liquid reservoir. The liquid may flow through the apparatus 100 with enough force and pressure to initiate the mixing process. When necessary, a pump may be used to generate said force and pressure. In this embodiment, the liquid may be actively pumped towards apparatus 100 of the system 600 of the present disclosure. The liquid may also be released using a passive system, such as located in a plume to treat the water before a water turbine or propeller.

In another embodiment, the treated source liquid is next passed through at least one filtration device 660. In a preferred embodiment, filtration device 660 reduces or substantially eliminates bacteria, viruses, cysts, and the like. Any filtration devices known in the art may be used. Filtration device 660 may include, but not limited to, particle filters, charcoal filters, reverse osmosis filters, active carbon filters, ceramic carbon filters, distiller filters, ionized filters, ion exchange filters, ultraviolet filters, back flush filters, magnetic filters, energetic filters, vortex filters, chemical oxidation filters, chemical addictive filters, Pi water filters, resin filters, membrane disc filters, microfiltration membrane filters, cellulose nitrate membrane filters, screen filters, sieve filters, or microporous filters, and combinations thereof. The treated and filtered liquid may be stored or distributed for use and consumption.

Before reaching the at least one filtration device 660, the treated liquid can optionally be passed through a zeta potential crystal generator (not shown). High zeta potential crystal generators are known in the art and generally useful for prevention or reduction of scaling. One known high zeta potential crystal generator is the Zeta Rod™ system. The Zeta Rod™ system increases zeta potential of crystals by electronically dispersing bacteria and mineral colloids in liquid systems, eliminating the threat of biofouling and scale and significantly reducing use of chemical additives. Colloids in liquid systems become components of the capacitor and receive a strong boost to their natural surface charge, altering double-layer conditions that govern particle interactions. Mineral scale formation is prevented as the Zeta Rod™ system stabilizes the dispersion of colloidal materials and suspended solids, preventing nucleation and attachment of scale to wetted surfaces. Bacteria remain dispersed in the bulk fluid rather than attaching to surfaces and cannot absorb nutrition or replicate to form slime and create foul odors. Existing biofilm hydrates excessively, loses bonding strength and disperses. Also, biological fouling, biocorrosion, and scale formation are arrested by the Zeta Rod™ system.

Another known high zeta potential crystal generator is the Sterling Water Anti-Scale Appliance manufactured by Sterling Water Systems, LLC, a subsidiary of Porta Via Water Company. As water passes through the Sterling Water Anti-Scale Appliance, an electrical current is discharged into the water, which decreases the water's surface tension and inhibits the formation of scale and hard water spots from appearing. The inhibition of scale formation is due to the increase of zeta potential of the treated water, which keeps mineral particles from encountering one another.

The treated liquid or treated fluid may be distributed to consumers or stored in a storage container, such as a reservoir. In this embodiment, before distribution of the stored treated liquid, the stored treated liquid may be passed through a second apparatus of the present disclosure. The once or twice or trice and so forth treated liquid is then distributed for use and consumption. It should be understood that the system may include one, two or more than 2 apparatuses (i.e. 3, 4, 5, 6, 7, 8, 9, 10 and so forth number of apparatuses), as such the trice or more times treated liquid may be then be distributed for consumption.

c. Method of Producing a Turbulent Solution

In one embodiment, the present disclosure relates to a method of mixing liquids or one or more liquids with one or more solids to form a mixture. The method, in one embodiment, may include passing one or more source liquids and/or one or more solids through an apparatus of the present disclosure thereby producing a mixed liquid.

In one step of the method, a source liquid may be passed through the apparatus 100. The source liquid may be passed at a suitable pressure such as about 3.2 bar. The pressure may be about 4 bar and the maximum pressure may be approximately 20 bar. The minimum pressure for the device of this disclosure to be effective is about 1 bar.

The critical material for the elements may be manufactured from a single metal, preferably corrosion resistant metal—for example stainless steel 300 series (for example 316L, 317L and so forth), or stainless steel 904L preferably stainless steels containing Mo.

There may be at least two elements in an apparatus of the present disclosure. In one embodiment, there may be a minimum of 2 elements in a small apparatus.

The applications include the homogenous mix of all polar and non-polar solutions. From water and listed chemicals for disinfection to gasoline, diesel fuel, bunder sea oil and also all lubrication and combustions oils.

The present disclosure relates also to a method of producing a liquid having a turbulent flow or of converting laminar flow to turbulent flow. The method includes passing a liquid, which may have a laminar flow through an apparatus of the present disclosure thereby producing a liquid with turbulent flow.

The present disclosure relates also to liquids created with an apparatus of the present disclosure and to liquids having turbulent flows produced with an apparatus of the present disclosure.

f. Applications

The inventive apparatus of the present disclosure and systems of the present disclosure are used to eliminate bacteria and microorganisms and to enhance the overall quality of liquid in several liquid systems. These liquid systems, described in more details below, may include, but are not limited to, water heaters, water coolers, potable water systems, food processing settings, molecule purification, household water filtration systems, sanitation settings, water softeners, ion exchangers, and medical, dental, and industrial water supply lines, Steam Assisted Gravity Drainage (SAGD), waste management and the like.

Water Heating Systems

In embodiments, the static apparatus of the present disclosure is integrated with various water heating systems. It has been unexpectedly discovered that water treated by a water heating system provided with the static apparatus of the present disclosure can eliminate bacteria and microorganisms in water, thereby improving the heat transfer efficiency of water heating systems. The liquid heating systems benefiting from the inventive system may include, but are not limited to, continuous water heaters, gas-fueled hot water tank type heaters, electric hot water tank type heaters, re-circulating hot water systems for hot water tanks, continuous water heaters, district heating systems, in-floor heating systems, heat exchangers that utilities hot water and/or steam, or in combination with heat transfer liquids, such as hot oils natural or synthetic.

Water Cooling Systems

In embodiments, the static apparatus of the present disclosure is integrated with various water-cooling systems. It has been unexpectedly discovered that water treated by a water-cooling system provided with a static apparatus of the present disclosure, improves cooling transfer efficiency. The water cooling systems may include, but are not limited to, continuous water coolers, refrigerators, gas and electrically fired evaporators, cooling pads, wet film evaporators, evaporative cooling systems, ground source cooling systems, lake or river water cooling systems, heat exchange cooling systems for lakes, grounds, rivers, or ocean waters, district cooling systems, re-circulating cooling systems, in-floor cooling systems, cooling towers all types makes and models, vacuum applications for industrial cooling on boilers, sugar plant cooking pans, paper mills, petroleum refining plants, mining plants, power plants including: coal, gas, oil, biomass, and nuclear.

The static apparatus of the present disclosure changes the physical properties of the liquid, lowers zeta potential, and lowers the viscosity of the water.

Potable Water Systems

In embodiments, the static apparatus of the present disclosure is integrated with various potable water systems. It has been discovered that water treated in system incorporating the static apparatus of the present disclosure, can enhance quality of water, as well as improving the taste of water. The potable water systems may include, but are not limited to, wells, springs, ponds, lakes, rivers, and the like. The static apparatus of the present disclosure changes the physical properties of the liquid, lowers zeta potential, and lowers the viscosity of the water.

The static apparatus of the present disclosure eliminates bacteria and microorganisms in water, thereby preventing the formation of biofilm in various piping systems, as well as improving the taste of water.

Food Processing Industry

It has been unexpectedly discovered that water treated by the static apparatus of the present disclosure can act as a disinfectant with the addition a minimal amount of chlorine (under 5 ppm) for storage of fresh produce. Since the treated water has been discovered to eliminate biofilm formation, food sanitation and production costs are lower and shelf life is lower. Further, since lower water surface tension increases solvency of the treated water, water treated in a system incorporating the static apparatus of the present disclosure, greatly increases the yield of oils from teas and coffees.

Sanitation Applications

Static apparatuses of the present disclosure can be integrated with sanitation systems such as swimming pools, power washers, car washes, household washing machines, commercial laundry facilities, household and commercial dishwashing facilities, and the like.

Water Treatment Applications

In embodiments, the static apparatus of the present disclosure can be integrated with water treatment applications such as water softeners, ion exchangers, all membrane and filter systems that utilize chlorine, chlorine dioxide, hydrogen peroxide, ozone, and the like.

Medical Industry

The static apparatus of the present disclosure can be integrated with medical systems and the systems are useful in increasing the turbulence of body fluids in humans and animals, and are useful also in applications related generally to skin treatments through bathing, spas, and daily usage, improved calcium uptake, improved teeth and conditions, as well as medical, dental, and industrial water lines.

Processed water on one pass through an apparatus of the present disclosure without filtration has exhibited the following results when used by human subjects: Reduction in Crohn's Disease Symptoms by more than 50%, reduction in inflammation of knee joints and muscle joints by more than 50%. Surprisingly a reduction of more than 50% in severe neuropathy and improvement in psoriasis has been seen within 14 days of a subject drinking the water processed with an apparatus of the present disclosure. This indicates that there is a change in the crystallization of the water with minerals and long term it also reduces the deposition of arterial plaque. Softer moisture skin and a reduction of eczema and psoriasis has been witnessed 100% of the time by all who have showered and bathed in the water.

Furthermore, there is a documented trail that scarring of tissue is reduced and healing of skin is accelerated.

Household Water Filtration Systems

The static apparatus of the present disclosure can be used in the common household and be integrated with any filtration device known in the art as described above.

Devices Incorporating the Static Apparatus of the Present Disclosure, Systems and Methods of the Present Disclosure Methods, generators and systems of the present disclosure can be used in conjunction with or retrofitted in existing devices and liquid distribution systems, such as water heating systems including, but are not limited to, continuous water heaters, gas-fueled hot water tank type heaters, electric hot water tank type heaters, re-circulating hot water systems for hot water tanks, continuous water heaters, district heating systems, in-floor heating systems, heat exchangers that utilities hot water and/or steam, or in combination with heat transfer liquids, such as hot oils natural or synthetic; water cooling systems including, but are not limited to, continuous water coolers, refrigerators, gas and electrically fired evaporators, cooling pads, wet film evaporators, evaporative cooling systems, ground source cooling systems, lake or river water cooling systems, heat exchange cooling systems for lakes, grounds, rivers, or ocean waters, district cooling systems, re-circulating cooling systems, in-floor cooling systems, cooling towers all types makes and models, vacuum applications for industrial cooling on boilers, sugar plant cooking pans, paper mills, petroleum refining plants, mining plants, power plants including: coal, gas, oil, biomass, and nuclear; potable water systems including, but are not limited to, wells, springs, ponds, lakes, rivers, and the like; food processing applications such as coffee and tea; sanitation systems including, but are not limited to, swimming pools, power washers, car washes, household washing machines, commercial laundry facilities, household dishwashers and commercial dishwashing facilities, and the like; water softeners; ion exchangers; all membrane and filter systems that utilize chlorine, chlorine dioxide, hydrogen peroxide, ozone, and the like; skin treatment systems through bathing, spas, and daily usage, improved calcium uptake, improved teeth and conditions; medical, dental, and industrial water lines; and any household water filtration systems.

Farms:

Animals, including dairy animals and poultry, that drink water treated with the static apparatus of the present disclosure may produce feces with less ammonia (ammonia was converted to organic nitrogen). Manure was changed stabilized and not producing methane or hydrogen sulfide.

Water Based Paint:

Paint manufactured with the static apparatus of the present disclosure display: faster drying times and had less volatile organic compounds, paint consumption due to better adhesion was reduced by 40 percent, paint demonstrated mold resistance, paint was brighter and dried smoother Beverage Plants:

Liquids treated with systems containing the static apparatus of the present disclosure of may replace the need for CIP (clean in place) for over 1 year in a beverage facility bottle cooling tunnels, spraying treated water on conveyors also removed biofilm in a matter of days.

Poultry Processing Plants:

Using processed water with systems having the static apparatus of the present disclosure in scalders allowed for the reduction of temperature by 3 to 5 degrees Fahrenheit. Birds came out noticeable cleaner.

Using water processed in accordance with the present disclosure in poultry chiller allowed birds to reach a 3-degree colder temperature with the same amount of refrigeration.

Chemicals

Chemicals processed through an apparatus of the present disclosure are more effective in measurable oxidation-reduction potential (ORP), Persistence, and in measurable coagulation and disinfection.

Removal of Heavy Metals from Protein Powers:

Water processed with the apparatus of the present disclosure separates on contact heavy metals from proteins such as iron, lead, manganese, arsenic and others. The reaction is substantially instantaneous and can be used in either a clarifier or a centrifugal separator.

The resulting dried protein material when added to treated water methodology can be used for all dried beverage materials including, teas, coffees, fruit concentrates, medicines, pharmaceuticals, starches, sugars, chocolate mixes, all flavour mixes and all food products including ground meats.

As such, another embodiment of the present disclosure is a method of removing/separating heavy metals from a protein powder, the method comprising contacting the protein powder with a liquid like water processed with a system of the present disclosure, thereby removing/separating the heavy metals from the protein powder.

The method of removing/separating heavy metals from powder protein may also include presoaking ungrounded protein-containing material in a suitable liquid treated with a system containing an apparatus of the present disclosure, like water, drying the presoaked material, grinding the protein-containing material, for example grinding the material to between a 70 and 100 mesh size, and re-washing the grounded protein-containing material in the treated liquid thereby separating the heavy metals from the grounded, protein-containing material. The method may also include spray drying the wet protein-containing material, regrinding the dried protein-containing material and re-washing the dried protein-containing material to separate finer heavy metals, spray drying the protein-containing material or using an alternative drying method. The protein obtained through the method hereby described will be substantially free of heavy metals. The heavy metals thereby separated may then be sold or used in other applications.

Ultra-Disinfection:

The treated water of the present disclosure may prevent the formation and/or dissolve biofilm with or without the addition of chemicals.

Air Disinfection and Filtration:

Men's urinal can be flushed or washed with water processed with an apparatus of the present disclosure. Ammonia of urine in restrooms may be converted on contact with the processed water in men's urinals to organic nitrogen therefore eliminating the ammonia vapors.

In a building in which the running water is treated with an apparatus of the present disclosure, dust may be reduced including biofilm on all surfaces such as glass, wood, tile, metals. Static Electricity is noticeably greatly reduced indoors in dusty and clean environments. Pet hair is observed by all to not be able to float in the air easily and dust always coagulated on all air filters in a uniform pattern.

Alcohol Manufacture:

Fermentation time of wines may be reduced by more than 50% with the use of water treated with the static apparatus of the present disclosure.

Less energy may be needed for production of ethanol and/or methanol. Production of ethanol may need up to about 17 percent less energy.

When treated water of the present disclosure is used in the dilution of alcohol it changes the chemical characteristics of the alcohol producing a finer smoother taste.

The treated liquid solution producing system of the present disclosure may be used to manufacture alcoholic beverages, including sake, vodka, scotch, rum, rye, gin, brandy, cognac, tequila, mezcal, wine, beers and so forth.

Ice Making:

A Vogt™ commercial ice maker made harder ice in a shorter time period. The machine made about 17 percent more ice.

Water Heating:

The water heats and dries with less energy at evaporates from surfaces up to about 30 percent faster.

Power Plant Applications:

In steam or thermal power plants improved efficiencies may be expected due to improved heat transfer, biofouling prevention of membranes and greater lubricity of the water treated with the apparatus of the present disclosure.

Condensing of steam turbines using cooling water can be closed looped using cooling towers and also will be greatly increased for efficiency.

Marine Transportation:

Treated liquids of the present disclosure may reduce friction on a ship's hull with our water.

Cleaning Devices:

The static apparatus of the present disclosure may be used in: power washers, car washes, laundry, carpet cleaning, steam cleaning, hot water cleaning.

Other applications include: injection of hydrogen gas into vegetable oils to reduce catalysis and to improve oil quality, use in bioreactors for methane production, elimination of ferric chloride in waste water due to aerobic condition of the waste water and a neutral pH of the waste water (currently this has been demonstrated in manure pits and is being validated in a food manufacturing facility. It has also been validated in the cooling tunnels with re-use water).

The mixtures of the present disclosure may be used in the following goods:

1) In water and water-related goods, including: bottled water, carbonated water, cologne water, drinking water, effervescent water, flat water, flavoured water, glacial water, iceberg water, mineral water, sparkling water, toilet water, vitamin enhanced water, water beds, water for spas, baths, whirlpools and swimming pools, water for the use in livestock and pet feeding, water for use in irrigation of vegetables, plants, trees, crops, water for use in the manufacture of solvents, water for use in the manufacture of paints, water for use in the purification of proteins, and water for use in the manufacture of detergents.

2) In dairy products including milk, milk products, evaporated milk, protein-enriched milk, cocoa beverages with milk, milk beverages containing fruits, cheese, sour cream, powdered milk, butter, cream, cheese spreads, soy-based cheese substitute, dairy cream, whipping cream, ice-cream, ice cream makers, soy-based ice-cream substitute.

3) In alcohol beverages, including alcoholic cocktails, alcoholic coffee-based beverages, alcoholic coolers, alcoholic fruit drinks, alcoholic lemonade, alcoholic malt-based coolers, beers, alcoholic tea-based beverages, sake, vodka, scotch, rum, rye, gin, brandy, cognac, tequila, mescal, wine.

4) In ice related products including ice, ice cube makers, ice packs, industrial ice.

5) In meats, including beef, pork, fish, poultry, frozen meat, smoked meat, canned meat.

6) In dental industry, including treated toothpaste, mouthwash, dental floss, dental gel, dental rinses, and denture cleaning preparations.

7) In the pharmaceutical/cosmetic industry, including eye washes, water for use in manufacturing cosmetics, water for use in manufacturing pharmaceuticals and medicinal products.

8) Steam, including steam generators, water for use in manufacturing steam, steam for use in extraction of oils from oil deposits, steam for use in Steam-assisted gravity drainage services.

9) Cleaning, including all-purpose cleaning preparations, carpet cleaning preparations, water for steam sanitation and steam cleaning, water for sanitation, water-based paints.

10) Oils, including anti-rust oil, auxiliary fluids for use with abrasives for the oil well industry, baby oil, bath oil, vegetable, mineral and animal oils, catalysts for use in oil processing, chemical additives for oil well drilling fluid, cooking oil, drilling fluids for oil and gas wells, drilling mud for oil well drilling, edible oil, fuel oil, heating oil, high pressure water jetting system for the gas and oil industry, industrial oil, insulating oil for transformers, motor oil, motor oil additives, oil for use in the manufacture of candles, oil for use in the manufacture of cosmetics, oil for use in the manufacture of paints, rubbing oil for wood, petroleum jelly, diesel fuel, aviation fuel, fuel additives, and fuel for domestic heating.

11) Proteins, protein for use as a food additive, protein for use as a food filler, nutritional supplements, water-processed animal and plant protein.

The mixtures of the present disclosure may preserve flavoring and essences for food. The encapsulation of flavors, fragrances and the like may serve to enhance or alter appearance of food and beverages. Used as a preservative, restore natural nutritional values through the addition of vitamins, minerals and proteins.

The mixtures of the present disclosure may be used to clean and eliminate pollutants found in edible birds' nests, for example removal of feathers, fungi, nitrates, nitrites and so forth. The mixtures of the present disclosure may make birds' nests more for manual removal of such contaminants while maintaining the original appearances of the nest and retain its nutrition and essences.

The apparatuses of the present disclosure may also be used in process, including waste water treatment, water and sewer management, water treatment, food sanitation, carpet cleaning, cleaning of buildings, diaper cleaning, dry cleaning, fur cleaning, jewelry cleaning, leather cleaning, rug cleaning, window cleaning, pool cleaning, automobile (car, trucks, buses, bikes, motorbikes and so forth) washes, train washes, ship washes, airplane washes, oil and gas well treatment, oil refining, fuel treatment, and steam-assisted gravity drainage.

The static spiral apparatus of the present disclosure provides an elegant novel solution to the problems mentioned in the Background by severely shearing the water and through the inversion of the sequential mixing discs creates a tremendous turbulence preventing dead zones and debris from collecting within the mixing device itself.

13) Waste Management

In embodiments, the apparatus of the present disclosure is used to facilitate the separation of waste oils from sludge, and to collect waste oil and lubricant materials for recycling. A variety of oil-in-water emulsions can be treated with the apparatus of the present disclosure to recover oil. Hydrocarbons and/or edible oils can be processed with the apparatus of the present disclosure. Oils in the emulsion and oil contaminated materials, include industrial lubricants, contaminated oils and waters, automotive/motor oils, lubricating oils and hydraulic oils. In embodiments, the recovered oils meet government and environmental regulated discharge approval.

A pump may be used to deliver oil-in-water emulsion obtained from a waste tank to an apparatus of the present disclosure in singular or in series of two, three, four, five, six, seven, eight, nine, ten, eleven, twelve, thirteen, fourteen, fifteen, sixteen, seventeen, eighteen to thirty and they can be also in parallel. The processed oil becomes separated from the water and can be recycled or returned back to a waste tank. In aspects the processed oil is a water-in-oil emulsion.

The purpose of this configuration is to allow for processing without re-circulation in a continuous stream to keep the fluid in suspension until it reaches an end destination or be placed in the tank again where it will self-separate according to specific gravity: silt on the bottom, heavy oils, water, light oils on the very top.

No other device may be necessary or can perform the function of the separation which is due to the intense shear of the fluid by the Spiral Static Mixer.

Prior to pumping the oil-in-water emulsion, the emulsion may be heated to aid in the processing.

In embodiments, chemicals may be used to assist in the separation if necessary, depending on the oil water emulsion.

All oil contains some water, so this is for all oil streams including refined oils, fuels, alcohols, ethanol, diesel and Bunker C type Fuels.

The process can also be used to desulfurization of oils and fuels.

14) Viscosity Reduction, Breaking Oil-in-Water Emulsions and Oil Cracking

There are many ways one can reduce the viscosity of oils, including heavy oils such as bitumen in oil sands and oil contaminated solutions. This may be necessary for enabling transportation of bitumen from the well to a refinery or the recycling of the oil in the oil contaminated solutions.

The apparatus of the present disclosure is used, in embodiments, to reduce the viscosity of oil containing liquid materials, such as oil-in-water emulsions, by breaking intermolecular bonding between the oil in the liquid material and the other components in the liquid material. By breaking the bonds between the oil and other substances in the material, the liquid material becomes less viscous. In addition, due to cracking that may be experienced by the oils in the material, smaller hydrocarbon chains have a lower viscosity.

In embodiments, the present disclosure relates to methods of breaking an oil-in-water emulsion. The method may be applied to any oil-in-water emulsions of any general type. An example of oil-in-water emulsions include oil-containing wastewater. The oil-in-water emulsion may also be part of a secondary oil recovery system. For example, oily wastewater from a plant can be broken using the method of the present disclosure to remove the oil in the oily waste from the water. In order to break the emulsion and remove the oil from the water, the emulsion stored in a tank is delivered to an apparatus of this disclosure, for example with the use of a pump, such as a positive displacement pump. If the emulsion is too dense, then prior to delivery to the apparatus, a less dense emulsion derivative may be obtained. To obtain the oil-in-water emulsion derivative, the original oil-in-water emulsion may first be pyrolyzed (in an oxygen deprived environment). The fumes that emanate are quenched with water resulting in an emulsification fluid. The emulsification fluid, also referred to as the emulsion derivative, is then delivered by a pump, such as a positive displacement pump, to an apparatus of the present disclosure. The emulsion or the emulsion derivative, as the case may be, is then passed through, or treated with, an apparatus of the present disclosure to obtain a processed material, whereby a separate aqueous phase and an oil containing phase is produced (see FIG. 8). All or substantially all of the oil in the processed material separates from the water and the oil can be removed from the water, permitting the clean water to be discarded and the oil to be recycled or discarded in an environmentally friendly manner for oil materials. The processed material includes a separate and distinct oil phase and an aqueous phase. The oil phase in the processed material is comprised of pure oil (i.e. about 100% oil) or is substantially comprised of pure oil in the form of a water-in-oil emulsion.

As such, in one embodiment, the present disclosure is a method of breaking an oil-in-water emulsion comprising passing the oil-in-water emulsion, or a derivative of the oil-in-water emulsion, through an apparatus of the present disclosure to obtain a processed material whereby a separate and distinct aqueous phase and oil phase is produced. In embodiments, the method may further include the step of separating the oil phase of the processed material from the water phase.

Cracking, or refining, is the overall reduction of lengths of hydrocarbon chains, a process that breaks or cracks the heavier, higher boiling-point petroleum fractions into more valuable products such as gasoline, fuel oil, and gas oils. In embodiments, the apparatus of the present disclosure is used to crack hydrocarbons contained in a source. Processed oil solutions or emulsions contain more hydrocarbons having shorter carbon chain species relative to untreated control oil solutions or emulsions before the process started, as well as losses of hydrocarbons having longer carbon chains relative to the control sample. The boiling point of the original, untreated liquid source is higher than the boiling point of the treated liquid thereby demonstrating the cracking of the untreated liquid source.

Most static mixer designs are meant for mixing two or more fluids either through division or homogenization. The device of this disclosure is designed primarily as a molecular shearing device. Its design gives it enough shearing strength to break both inter (weak molecular bonds) and intra (strong molecular bonds). The apparatus of the present disclosure has clearly demonstrated the ability to break both inter and intra molecular bonds with a water oil emulsion. Independent of the emulsion constituents there is always both an inter and intra molecular bond separation. This separation results in the fluid consistently separating into its separate components by either specific gravity or into a filterable suspension. Furthermore, fluids can be processed to a desired separation by Specific Gravity Fluid Tank Separation or Gas Chromatography Analysis given enough processing time and pressure. For instance, a C-40 Oil can be reduced to smaller chains by the length of time and fluid pressure force of processing. This results in a change in viscosity and chemical composition of the mixture. This is far beyond what a traditional static mixer was ever imagined to be able to achieve.

The apparatus of the present disclosure changes the existing paradigm of breaking oil emulsions either using solvents and/or heat distillation extraction. This device requires no heat, ultrasound or solvents to break inter and intra molecular bonds and separate water from an oil emulsion. The apparatus of the present disclosure is an ultra-low energy method of separating oil from water so that the carbon footprint in traditional petroleum industry can be dramatically reduced. It can be referred to as Low Energy Refining. In separating emulsions temperatures have ranged from 15 Degrees Celsius to 21 Degrees Celsius which were the ambient conditions. Less energy is needed to pump the oil water emulsion in our tests we demonstrated greater than a 50% reduction in pumping energy due to the decreased viscosity of the fluid.

Also, in the treatment of water that is contaminated with Hydrocarbons or Fluorocarbons or also more difficult compounds such as Perfluorooctyl Sulfonate (PFOS). Without this distinct water oil emulsion separation, it is extremely difficult to filter out or mechanical separate these complex chemicals.

EXAMPLES

The examples are described for the purposes of illustration and are not intended to limit the scope of the disclosure.

Example 1

In experiments to date the new static apparatus was able to dissolve biofilms in plumbing systems by converting the flow from laminar to a turbulent flow. The water remains turbulent even after filtration (even after 9 filters) and flows faster in water system testing to date. In filtration there is a complete elimination of biofouling and a total utilization of the filter media because the gases in the system have been converted into smaller gas structures that promote flow, speed of flow and increase pressure.

Example 2

Bottled water and bottled water processed through the apparatus of the present disclosure were boiled in a Breville® electric pot. After boiling the water was discarded. Mineral deposit can be seen at the bottom of the pot for unprocessed bottled water. No mineral deposits are seen at the bottom of the pot for processed bottled water.

The apparatus of the present disclosure prevents the formation of crystals by lowering the Z potential, thereby eliminating crystallization.

Example 3

The petroleum refining industries generate considerable amounts of sludge and tank bottoms as waste. Crude oil storage tanks are an essential part of all major operations in the petroleum industry. Petroleum refinery receives crude oil containing emulsified water and solids. As the crude oil storage tanks are repeatedly filled and emptied, the water and solids settle towards the bottom as sludge. For tanks that have been in service for several years, the sludge accumulation becomes several feet deep, results in a loss of ullage in refinery crude storage tanks. The refinery sludge waste is categorized as hazardous waste.

Due to the solids content of crude oil, those tanks loose storage capacity over the years, as they slowly fill up with settled solids from the crude. Those tanks therefore require regular cleaning in order to maintain their storage capacity. Tanks are emptied of crude oil and the residual sediment and residues adhering to the tank walls are then removed with high pressure water jets. The resulting product is characterized by containing a considerable amount of water content (in the order of 30-60% by volume), an oil phase with rather high viscosity, typically the presence of an emulsified phase, and high solids content (in the order of 10-40% by volume).

The apparatus of the present disclosure can be used to maximize the waste oil recovery from sludge and tank bottoms and to minimize the volume of the hazardous waste.

Methodology

The bottom tank sludge is pyrolyzed (in an oxygen deprived environment). The fumes that emanate are quenched with water resulting in an emulsification fluid.

The emulsification fluid (about 20,000 Gallons) is delivered by a Positive Displacement Pump to a 1.5 inch (about 3.81 cm) inlet and outlet fitting size and 2-inch (about 5.08 cm) diameter of the body apparatus of the present disclosure (25-30 GPM). The processed oil is then returned to emulsification tank.

The Processing:

Processing involves three things: (1) flow/Pressure, (2) viscosity modification, and (3) separation of the fluids as a result of inter and intra molecular bonding shifts into specific gravity weight fluids as follow:

Top Layer: Light oils and carbon chains (2) Second Layer: Water (3) Third Layer: Heavier Oil (4) Fourth Layer: Heaviest Oils (5) Fifth Layer: Inorganics (Ash, Silt and others)

5 grams of the sludge failed to burn under a hood. On the other hand, 5 grams of processed oil was burnt under a fume hood for about 2 minutes, After burning, 3.4 grams remained, thereby showing that at least 1.8 grams of the processed oil included volatiles.

Figure 8:
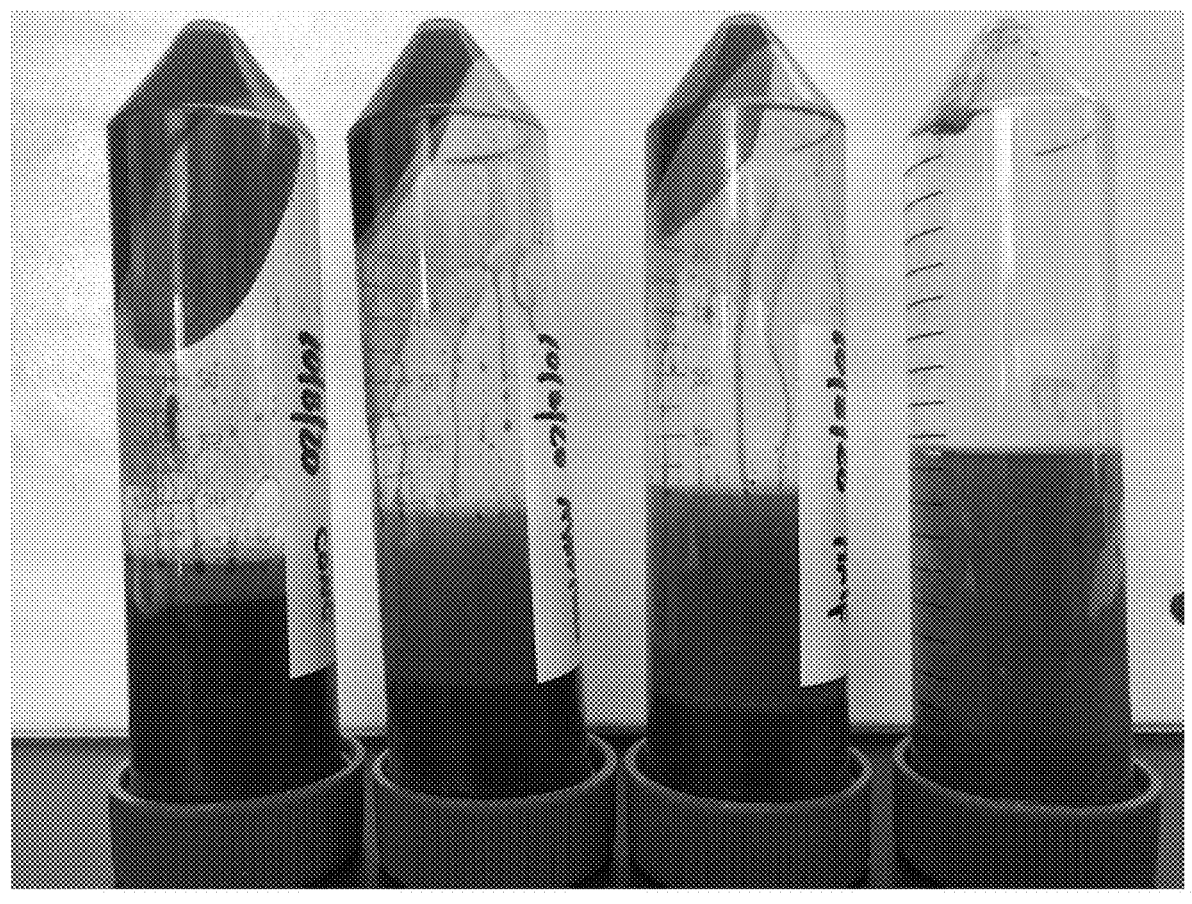
FIG. 8. Photograph of centrifuge tubes containing emulsions processed with the reverse flow apparatus of the present disclosure. The emulsions were taken from different levels of a waste tank. The sample in the first tube from the left was taken from a cone at the bottom of a waste tank, while the fourth tube from the left is taken from the top of the waste tank.

The photographs of FIG. 8 illustrate oil separation from an aqueous phase. As It can be seen, the apparatus of the present disclosure separates oil from water even From samples taken from the cone at the bottom tank, which is the most viscous sludge of the tank.

In addition, the viscosity of the oil was reduced independent of the carbon length being C40 or C20. The pump flow more than doubled at temperatures of 15 to 21 degrees Celsius.

Example 4

A subject that suffers of neuropathy and psoriasis had an apparatus of the present disclosure installed in his house so that all running water in the house is treated by the apparatus. The subject drank and showered with water treated with an apparatus of the present disclosure for two weeks. After two weeks the subject neuropathy and psoriasis improved. The subject now can feel his toes (which were numbed) and have control of his toes. From showering in the water, the psoriasis decreased by more than 60% after two weeks of treatment.

The above disclosure generally describes the present disclosure. Changes in form and substitution of equivalents are contemplated as circumstances may suggest or render expedient. Although specific terms have been employed herein, such terms are intended in a descriptive sense and not for purposes of limitation. Other variations and modifications of the disclosure are possible. As such modifications or variations are believed to be within the sphere and scope of the disclosure as defined by the claims appended hereto.

What is claimed is:

1. A reversing flow apparatus comprising a chamber having a series of two or more sequential rings mounted on a shaft extending axially through the chamber, the rings being separated by a space, each ring comprising a circumference and one or more S-shaped members extending from a point in the circumference to another point in the circumference and across a center of the ring, the two or more sequential rings being mounted along the shaft in a twist arrangement such that at least one ring in the apparatus has its S-shaped member in a forward-facing position and at least one ring in the apparatus has its S-shaped member in a reverse-facing position.

2. The reversing flow apparatus of claim 1 further comprising a housing having an inflow portion for receiving one or more untreated liquids, a treatment portion containing the chamber for treating the one or more untreated liquid, and an outflow portion for releasing the treated one or more liquids.

3. The reversing flow apparatus of claim 1, wherein the two or more rings are made of a metal or a combination of metals.

4. The reversing flow apparatus of claim 3, wherein the rings are made of stainless-steel containing molybdenum (Mo).

5. The reversing flow apparatus of claim 1, wherein the rings are made of a metal alloy comprising from about 3.0 wt. % to about 4.0 wt. % molybdenum.

6. The reversing flow apparatus of claim 1, wherein each ring is formed from a disc cut to form the one or more S-shaped members.

7. A system for treating liquid solutions or emulsion, the system including a source of the liquid solution or emulsion and a reversing flow apparatus of claim 1, the inflow portion of the reversing flow apparatus being operatively connected to the source.

8. The system of claim 7, wherein the system further comprises at least one of a filtration device, a UV sterilizer and a Z potential crystal generator, wherein the reversing flow apparatus, the source and the at least one of the filtration device, the UV sterilizer and the Z potential crystal generator are in liquid communication with one another.

9. The system of claim 7, wherein the system further comprises a filtration device, a UV sterilizer and a Z potential crystal generator, wherein the reversing flow apparatus, the source, the filtration device, the UV sterilizer and the Z potential crystal generator are in liquid communication with one another.

10. The system of claim 7, wherein the system comprises multiple reversing flow apparatuses according to claim 1.

11. A method producing a mixed solution of liquids or of one or more liquids with one or more solids, the method comprising passing the liquids to be mixed or the one or more liquids and the one or more solids to be mixed through the reversing flow apparatus of claim 1, thereby producing the mixed solution.

12. The method of claim 11, wherein the one or more liquids includes a gas.

13. The method of claim 12, wherein the gas include nitrogen, oxygen, carbon dioxide, ozone, ethanol, methanol, hydrogen or combinations thereof.

14. The method of claim 11, wherein the one or more liquids are optionally passed, before or after the reversing flow apparatus, through at least one filtration system.

15. A method of converting laminar flow to turbulent flow, the method comprising passing a liquid with laminar flow through the reversing flow apparatus of claim 1.

16. A liquid or emulsion processed with the reversing flow apparatus of claim 1.

17. A method of breaking an oil-in-water emulsion, the method comprising passing the oil-in-water emulsion though the reversing flow apparatus of claim 1 to obtain a processed material whereby a separate aqueous phase and oil phase is produced.

18. The method of claim 17, wherein the method further comprises pyrolyzing the oil-in-water emulsion to obtain a derivative, and wherein the method comprises passing the derivative through the reversing flow apparatus instead of the oil-in-water emulsion.

19. The method of breaking the oil-in-water emulsion of claim 17, wherein the oil-in-water emulsion is oily wastewater, a petroleum feedstock or a part of a secondary oil recovery system.

20. A method of lowering the viscosity of liquid solution or emulsion containing oil, the method comprising passing the liquid solution or emulsion containing oil through the reversing flow apparatus of claim 1 to obtain a processed material having lower viscosity than the liquid solution or emulsion containing oil, thereby lowering the viscosity of the liquid solution or emulsion containing oil.

21. A method of lowering the boiling point of an original liquid source having kerogens, long-chain hydrocarbons or a mixture thereof, the method comprising passing the original liquid source through the reversing flow apparatus of claim 1 to obtain a treated material, wherein the boiling point of the original liquid source is higher than the boiling point of the treated liquid.

22. A method of cracking a liquid comprising passing the liquid through the reversing flow apparatus of claim 1 to obtain a cracked liquid.

23. The method of cracking a liquid of claim 22, wherein the cracked liquid contains more hydrocarbons having shorter carbon chain species relative to the liquid.

24. The method of cracking a liquid of claim 22, wherein the method is devoid of solvents.

25. The method of cracking a liquid of claim 22, wherein the liquid is an emulsion, a petroleum feedstock or a part of a secondary oil recovery system.

26. A method of treating Crohn's Disease, a neuropathy or reducing inflammation of knee joints in a subject, comprising administering to the subject a liquid processed through the reversing flow apparatus of claim 1.

* * * * *